US00PP33971P2

(12) United States Plant Patent
Trees

(10) Patent No.: US PP33,971 P2
(45) Date of Patent: Feb. 22, 2022

(54) ***SALVIA* PLANT NAMED 'BALSALUCHL'**

(50) Latin Name: ***Salvia* hybrid**
Varietal Denomination: Balsaluchl

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/501,791

(22) Filed: Oct. 14, 2021

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Salvia* plant named 'Balsaluchl', characterized by its light violet-blue colored flowers, dark green-colored foliage, and vigorous, upright-compact growth habit, is disclosed.

1 Drawing Sheet

Latin name of genus and species of plant claimed: *Salvia* hybrid.

Variety denomination: 'Balsaluchl'.

BACKGROUND OF THE INVENTION

The present invention relates to a new and distinct cultivar of *Salvia* plant botanically known as *Salvia* hybrid and hereinafter referred to by the cultivar name 'Balsaluchl'.

The new *Salvia* hybrid cultivar is an irradiation-induced sport of Mystic Spires 'Balsalmispim', U.S. Plant Pat. No. 29,604, characterized by its light violet-colored flowers, dark green-colored foliage, and vigorous, upright-compact growth habit. The irradiation occurred during May 2019. The new cultivar was discovered as a side shoot and selected during September 2019 in a controlled environment in Arroyo Grande, Calif.

Asexual reproduction of the new cultivar by terminal stem cuttings since September 2019 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsaluchl' as a new and distinct cultivar of *Salvia* plant:

1. Light violet-blue colored flowers;
2. Dark green-colored foliage; and
3. Vigorous, upright-compact growth habit.

Plants of the new cultivar differ from plants of the parent primarily in having lighter violet-blue colored flowers, smaller sized corollas, and smaller sized leaves.

Of the many commercially available *Salvia* cultivars, the most similar in comparison to the new cultivar is Mysty 'Balsalmysty', U.S. Plant Pat. No. 29,605. However, in side-by-side comparisons, plants of the new cultivar differ from plants of 'Balsalmysty' in at least the following characteristics:

1. Plants of the new cultivar have lighter violet-blue colored flowers than plants of 'Balsalmysty';
2. Plants of the new cultivar have smaller sized corollas, as measured by width and length, than plants of 'Balsalmysty'; and
3. Plants of the new cultivar have smaller sized leaves than plants of 'Balsalmysty'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsaluchl'. The plants were approximately 4.5-months old. The plants were grown in 3-gallon containers for approximately 11 weeks in an outdoor nursery in West Chicago, Ill. Plants were pinched twice prior to transplant.

DETAILED BOTANICAL DESCRIPTION

Figure 1:
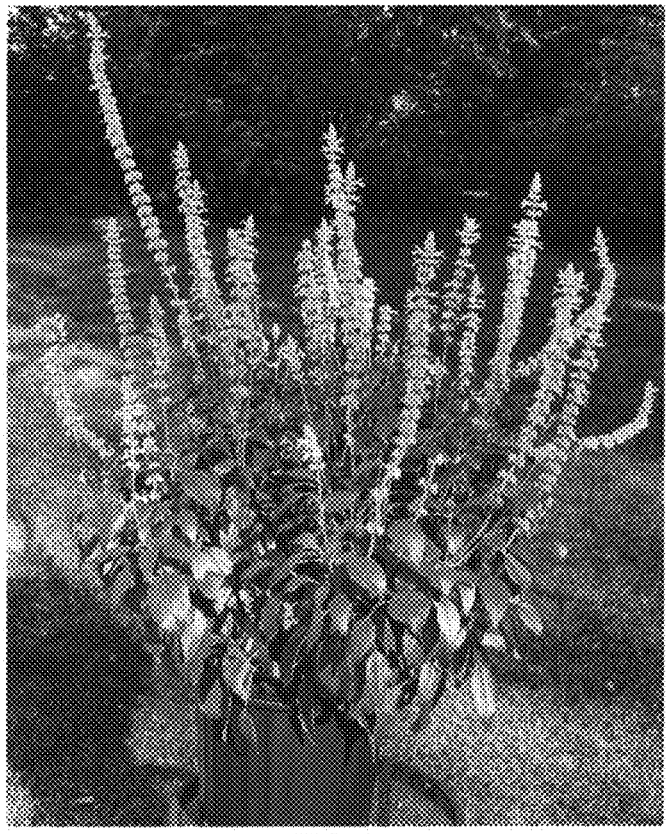
FIG. 1 illustrates a side view of the overall growth and flowering habit of 'Balsaluchl'.
Figure 2:
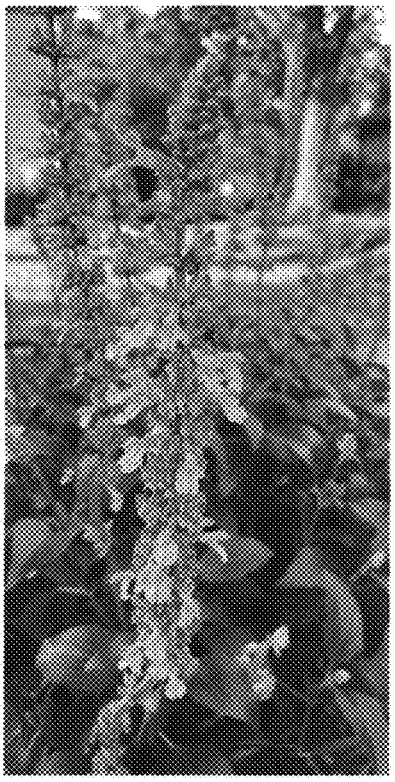
FIG. 2 illustrates a close-up view of an inflorescence of 'Balsaluchl'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately 4.5-month-old plants produced from cuttings from stock plants and grown under conditions comparable to those used in commercial practice. The plants were grown in 3-gallon containers for approximately 11 weeks in an outdoor nursery in West Chicago, Ill. Plants were given two pinches prior to transplant. Prior to transplant plants were grown in a polycarbonate greenhouse in West Chicago, Ill. Greenhouse temperatures were maintained at approximately 70° F. to 85° F. (21° C. to 29° C.) during the day and approximately 60° F. to 70° F. (16° C. to 21° C.) during the night. Supplemental lighting was used during propagation stage. Measurements and numerical values represent averages of typical plants.

Botanical classification: *Salvia* hybrid 'Balsaluchl'.

Parentage:

*Parent.*—Mystic Spires 'Balsalmispim', U.S. Plant Pat. No. 29,604.

Propagation:

*Type cutting.*—Terminal stem.

*Time to initiate roots.*—Approximately 5 to 8 days.

*Time to produce a rooted cutting.*—Approximately 21 to 42 days.

*Root description.*—Fine, fibrous.

*Rooting habit.*—Freely branching.

Plant description:

*Commercial crop time.*—Approximately 6 to 10 weeks from a rooted cutting to finish in a 15 cm pot.

*Growth habit and general appearance.*—Annual, vigorous, upright-compact growth habit.

*Size.*—Height from soil level to top of plant plane: Approximately 91.5 cm. Width: Approximately 90.0 cm.

*Branching habit.*—Freely branching. Pinching enhances lateral branching. Quantity of branches per plant: Approximately 6.

*Branch.*—Shape: Square in cross section. Strength: Strong. Length to base of inflorescence: Approximately 34.0 cm. Diameter: Approximately 5.0 mm to 8.0 mm. Length of central internode: Approximately 4.5 cm. Texture: Densely pubescent with short hairs. Color of pubescence: NN155C. Color of young and mature stems: 144A occasionally with edges of N186A, color appears lighter due to pubescence.

Foliage description:

*General description.*—Quantity of leaves per main branch: Approximately 6 to 8. Fragrance: Slight, sage-like. Form: Simple. Arrangement: Opposite.

*Leaves.*—Aspect: Petiole acute to perpendicular angle to stem, leaf blade becomes obtuse angle with age. Shape: Ovate. Margin: Serrate. Apex: Acute. Base: Obtuse. Venation pattern: Pinnate. Length of mature leaf: Approximately 7.2 cm. Width of mature leaf: Approximately 4.3 cm. Texture of upper surface: Moderately pubescent with short, fine hairs. Texture of lower surface: Densely pubescent on venation only. Color of upper surface of young and mature foliage: 137A with 139A and venation of 146D. Color of lower surface of young and mature foliage: Closest to 137B with venation of 147D.

*Petiole.*—Length: Approximately 2.5 cm to 3.2 cm. Diameter: Approximately 2.0 mm. Texture: Densely pubescent with short, appressed hairs. Color of pubescence: NN155C. Color: 147D with 137B, color appears lighter due to pubescence.

Flowering description:

*Flowering habit.*—'Balsaluchi' is freely flowering under outdoor growing conditions with substantially continuous blooming from spring through autumn and year-round in greenhouse environment.

*Lastingness of individual floret.*—Approximately 4 to 5 days.

Inflorescence description:

*General description.*—Type: Spikes in verticillaster arrangement, florets in clusters of approximately 7, not persistent, often slightly curved with age. Quantity of inflorescences per plant: Approximately 40. Fragrance: Faint, sweet. Length or height of inflorescence: Approximately 15 cm to 41.0 cm. Width of inflorescence: Approximately 4.0 cm. Quantity of fully-open flowers per inflorescence: Approximately 23, one to two per cluster open at one time.

*Peduncle.*—Shape: Square in cross section. Strength: Strong. Aspect: Erect. Length: Approximately 8.0 cm to 16.0 cm. Diameter: Approximately 3.0 mm. Texture: Densely pubescent with short hairs. Color of pubescence: NN155C. Color: 144A with edges of N186A, color appears lighter due to pubescence.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 7.0 mm. Diameter: Approximately 3.0 mm. Texture: Densely pubescent with short, appressed hairs. Color of pubescence: NN155C. Color: Calyx of 144A, color appears lighter due to pubescence, and petal portion of 90A.

*Corolla.*—Shape: Bilabiate, lower lip having three lobes, base fused. Width: Approximately 9.0 mm. Length: Approximately 8.0 mm. Depth: Approximately 1.8 cm.

*Upper lip.*—Shape: Hooded. Margin: Entire. Apex: Rounded. Length from throat: Approximately 5.0 mm. Width: Approximately 4.0 mm. Texture of inner surface: Glabrous. Texture of outer surface: Densely pubescent. Color of pubescence: 92B to 92C. Color of inner and outer surface when first and fully open: 92C to 92D.

*Lower lip.*—Shape of central lobe: Obovate. Margin: Entire. Apex of central lobe: Emarginate. Apex of lateral lobes: Rounded. Length from throat of central lobe: Approximately 9.0 mm. Width of central lobe: Approximately 9.0 mm. Length from throat of lateral lobes: Approximately 5.0 mm. Width of lateral lobes: Approximately 2.0 mm. Texture of upper surface: Glabrous. Texture of lower surface: Moderately pubescent. Color of upper and lower surface when first and fully open: 92C to 92D.

*Corolla tube.*—Length: Approximately 7.0 mm. Diameter at opening: Approximately 3.0 mm. Diameter at base: Approximately 1.0 mm. Texture of inner and outer surfaces: Glabrous. Color of inner and outer surface when first and fully open: 92D.

*Calyx.*—Shape: Tubular. Length: Approximately 6.0 mm. Diameter: Approximately 4.0 mm.

*Sepals.*—Quantity per flower: Fused into two lobes. Shape: Obovate. Apex: Upper lobe acute, lower lobe notched. Length: Approximately 6.0 mm. Width of lobes: Approximately 4.0 mm. Texture of inner surface: Glabrous. Texture of outer surface: Densely pubescent with short, appressed hairs. Color of pubescence: NN155C. Color of inner surface: 144A. Color of outer surface: 144A, color appears lighter due to pubescence.

*Bracts.*—Quantity: One bract located at the base of each floret cluster. Length: Approximately 8.0 mm. Width: Approximately 8.0 mm. Texture of inner surface: Glabrous. Texture of outer surface: Densely pubescent with short, appressed hairs. Color of pubescence: NN155C. Color of inner surface: 144A. Color of outer surface: 144A, color appears lighter due to pubescence.

*Pedicel.*—Strength: Strong, flexible. Aspect: At an acute angle. Length: Approximately 2.0 mm. Diameter: Approximately 1.0 mm. Texture: Densely pubescent with short, appressed hairs. Color of pubescence: NN155C. Color: 144A, color appears lighter due to pubescence.

*Reproductive organs.*—Androecium: Stamen quantity: 2 per flower, dorsifixed, strongly curved. Stamen length: Approximately 7.0 mm. Filament length: Approximately 6.0 mm. Filament color: NN155D tinted with 90C on lower half, opaque. Anther shape: Oblong. Anther length: Approximately 1.0 mm. Anther color: 12B transitioning to N199C at dehiscence. Pollen amount: Abundant. Pollen color: 12C. Gynoecium: Pistil quantity: 1 per flower. Pistil length: Approximately 1.4 cm. Stigma shape: Cleft, two-parted. Stigma length: 2.0 mm. Stigma color: NN155D, tinted with 92B. Style length: Approximately 1.0 cm. Style color: NN155D, opaque. Style texture: Glabrous with a vertical line of feather-like pubescence of NN155D tinted with 92B extending from the stigma for approximately 5.0 mm. Ovary length: Approximately 2.0 mm. Ovary color: 154D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balsaluchl', substantially as herein illustrated and described.

* * * * *